(12) United States Patent
Schomberg

(10) Patent No.: US 7,342,992 B2
(45) Date of Patent: Mar. 11, 2008

(54) X-RAY APPARATUS PROVIDED WITH A POSITIONALLY ADJUSTABLE X-RAY DETECTOR

(75) Inventor: Hermann Schomberg, Hamburg (DE)

(73) Assignee: Koninklijke Philips Electronics, N.V., Eindhoven (NL)

( * ) Notice: Subject to any disclaimer, the term of this patent is extended or adjusted under 35 U.S.C. 154(b) by 82 days.

(21) Appl. No.: 10/507,200

(22) PCT Filed: Mar. 10, 2003

(86) PCT No.: PCT/IB03/00829

§ 371 (c)(1),
(2), (4) Date: Sep. 9, 2004

(87) PCT Pub. No.: WO03/075763

PCT Pub. Date: Sep. 18, 2003

(65) Prior Publication Data

US 2006/0023830 A1    Feb. 2, 2006

(30) Foreign Application Priority Data

Mar. 13, 2002    (DE) ............................... 102 11 016

(51) Int. Cl.
*G01N 23/083* (2006.01)
(52) U.S. Cl. ...................................................... 378/19
(58) Field of Classification Search ............... 378/57, 378/140, 141, 142, 199, 203, 119, 121, 98.8, 378/196–198, 4–20
See application file for complete search history.

(56) References Cited

U.S. PATENT DOCUMENTS 4,541,293 A * 9/1985 Caugant et al. ............ 74/89.18
6,075,837 A * 6/2000 Roos et al. ................. 378/98.2
2003/0091156 A1 * 5/2003 Crain et al. ................. 378/197

FOREIGN PATENT DOCUMENTS

DE    10008053 A1 *   9/2001
JP    11226001         8/1999

OTHER PUBLICATIONS

Jaffray et al., "Flat-Panel Cone-Beam Computed Tomography for Image-Guided Radiation Therapy," 2002, Int. J. Rad. Onc. Biol. Phys., vol. 53, No. 5, pp. 1337-1349.*

* cited by examiner

*Primary Examiner*—Edward J. Glick
*Assistant Examiner*—Anastasia S. Midkiff

(57) ABSTRACT

The invention relates to an X-ray apparatus which includes an X-ray source (2) for the emission of a conical X-ray beam and an X-ray detector (3) for the multiple detection of the X-rays after their passage through an object to be examined, being arranged along an object axis (4), while the X-ray source (2) and the X-ray detector (3) are displaced along a trajectory. In order to increase the size of the reconstructable examination zone without increasing the size of the X-ray detector, and in order to minimize the problem caused by projections truncated in the transverse direction, the invention proposes an X-ray apparatus which includes means (12, 14, 15) for changing the position and/or the orientation of the X-ray detector (3) relative to the X-ray source (2) and a control unit (11) for displacing the X-ray source (2) and the X-ray detector (3) along the trajectory and for controlling the position and/or the orientation of the X-ray detector (3) during the detection of the X-rays.

20 Claims, 3 Drawing Sheets

X-RAY APPARATUS PROVIDED WITH A POSITIONALLY ADJUSTABLE X-RAY DETECTOR

Figure 1A:
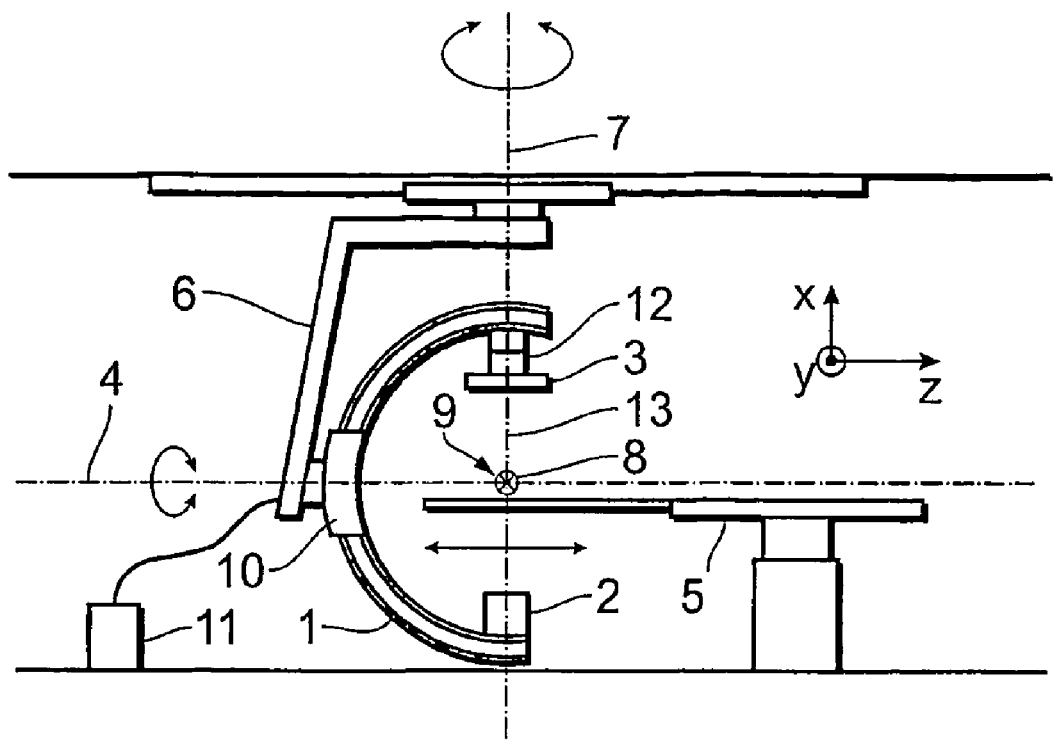

The invention relates to an X-ray apparatus which includes an X-ray source for the emission of a conical X-ray beam and an X-ray detector for the detection of the X-rays after their passage through an object to be examined, being arranged along an object axis, while the X-ray source and the X-ray detector are displaced along a trajectory. The invention also relates to a corresponding method of forming X-ray images as well as to a computer program for the execution of the method. The invention relates in particular to a C-arm X-ray system comprising a flat, rectangular X-ray detector.

An X-ray apparatus of this kind is generally known and is often used for the formation of X-ray images. The X-ray source and the X-ray detector thereof are usually attached to a C-arm so as to face one another and are moved along a predetermined trajectory around an object to be examined, notably a patient, for the acquisition of cone beam projections of the examination zone of the object to be examined. A 3D image of the examination zone can be reconstructed from the cone beam projections thus acquired. Analog X-ray image intensifiers having a circular detector surface are often used as the X-ray detector. In future, however, use will increasingly be made of digital flat X-ray detectors having a rectangular, not necessarily square detector surface.

JP 11226001 A discloses a C-arm X-ray apparatus having a flat X-ray detector which can be rotated around a plane of rotation which extends perpendicularly to the detector surface and through the center thereof in order to compensate an adjusting angle of the L-arm of the C-arm X-ray system, thus ensuring that the orientation of the X-ray detector is always the same during the detection of the X-rays.

U.S. Pat. No. 4,541,293 discloses an X-ray apparatus in which the X-ray source is arranged on a curved rail member so as to be displaceable relative to a stationary X-ray detector, thus enabling the execution of special X-ray examinations.

It is an object of the invention to maximize the dimensions of the reconstructable examination zone without increasing the dimensions of the X-ray detector. Moreover, truncated projections in the direction transversely of the object axis should be avoided as much as possible so as to achieve an as high as possible image quality of the reconstructed images.

This object is achieved in accordance with the invention by means of an X-ray apparatus of the kind set forth which is characterized in that it includes means for changing the position and/or the orientation of the X-ray detector relative to the X-ray source and also a control unit for displacing the X-ray source and the X-ray detector along the trajectory and for controlling the position and/or orientation of the X-ray detector during the detection of the X-rays.

The invention is based on the idea that for many trajectories, for example, as described in German patent application 100 63 442.7 (PHDE 000232), it is advantageous to change the position and/or the orientation of a rectangular X-ray detector relative to the X-ray source during the detection of the X-rays, that is, in such a manner that the examination zone that can be reconstructed is maximized. The control of the position and/or orientation of the X-ray detector is then provided by a suitable control unit, the exact control being dependent on various factors such as, for example, the course of the trajectory and the ratio of the edges of the sensitive detector surface of the X-ray detector.

Advantageous embodiments of the X-ray apparatus in accordance with the invention are disclosed in the dependent claims. Claim 10 describes a method of forming X-ray images by means of an X-ray apparatus in accordance with the invention. The invention also relates to a computer program with programming means for making a computer control an X-ray apparatus as claimed in claim 1 in conformity with the method in accordance with the invention when the computer program is executed on a computer. A first advantageous embodiment of the X-ray apparatus in accordance with the invention utilizes a flat, rectangular X-ray detector which is rotatable around the connecting line between the focal point of the X-ray source and the center of the X-ray detector. The control unit is constructed in such a manner that one of the edges of the rectangular X-ray detector extends at right angles to the object axis during the detection of the X-rays. Because flat X-ray detectors usually do not have a square shape, the orientation of the X-ray detector is thus controlled in such a manner that either the short or the long edges of the rectangular X-ray detector extend at right angles to the object axis, that is, for example, at right angles to the longitudinal axis of the patient in the case of an examination of a patient who is arranged on a patient table.

Preferred further versions of this embodiment are disclosed in the claims 3 and 4. For many trajectories it suffices to adjust the desired orientation of the X-ray detector prior to the beginning of the displacement and to keep it constant during the displacement. For other trajectories the orientation of the X-ray detector must be continuously changed during the completion of these trajectories.

The means for changing the position and/or the orientation of the X-ray detector in a second embodiment in accordance with the invention are constructed in such a manner that the angle between the central X-ray of the X-ray beam and the connecting line extending between the focal point of the X-ray source and the center of the X-ray detector can assume a value other than zero, and that the control unit is constructed in such a manner that at least two different angular positions are adjusted during the detection of the X-rays.

This embodiment enables the use of a smaller X-ray detector while nevertheless achieving the effect of a larger X-ray detector, that is, X-ray projections from a larger number of positions than in the case of a small X-ray detector which is arranged in a fixed position. Overall the examination zone can thus be increased further, so that the problem posed by the truncated projections is also reduced.

Preferred further versions of this embodiment are disclosed in the claims 6 to 9. Therein, the X-ray detector is mounted on one or more rails in order to change its position and/or orientation. Preferably there is provided a rail which enables the X-ray detector to be shifted out of the plane of the C-arm in the lateral direction. However, shifting of the X-ray detector within the plane of the C-arm is also feasible, notably in the direction of the C-arm. The rail may also be constructed so as to be straight, but is preferably curved around the focal point of the X-ray source in order to achieve optimum alignment of the X-ray detector relative to the X-ray source. It is thus achieved notably that an anti-scatter grid, which is preferably attached to the X-ray detector, always remains focused on the X-ray source.

In accordance with the further embodiment in conformity with claim 9, it is also advantageously arranged that each trajectory is completed a number of times, the X-ray detector being displaced to a different angular position for each run, that is, so that it has a different position and/or orientation relative to the X-ray source. This allows X-ray projections to be acquired from the desired different directions, thus enabling the reconstruction of an as large as possible examination zone.

The steps proposed in the claims 2 and 5 can also be advantageously taken in combination in an X-ray apparatus.

Figure 5:
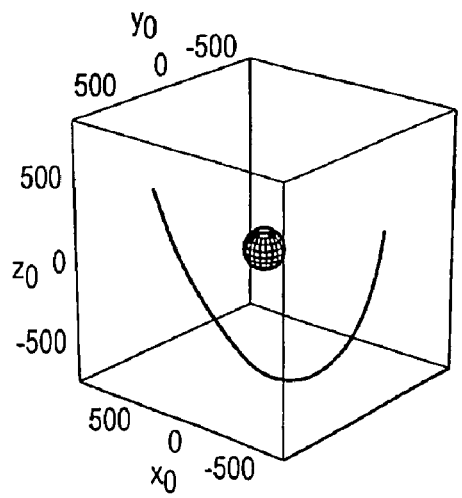
Figure 6:
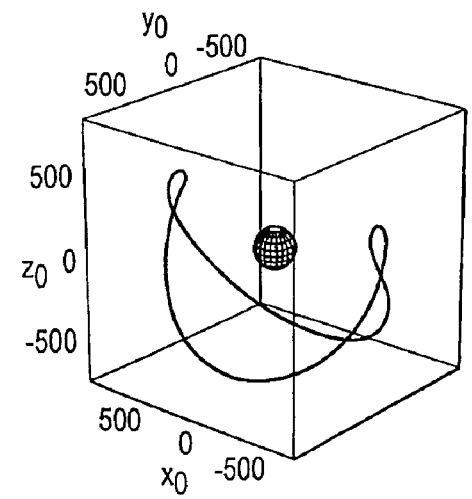
Figure 7:
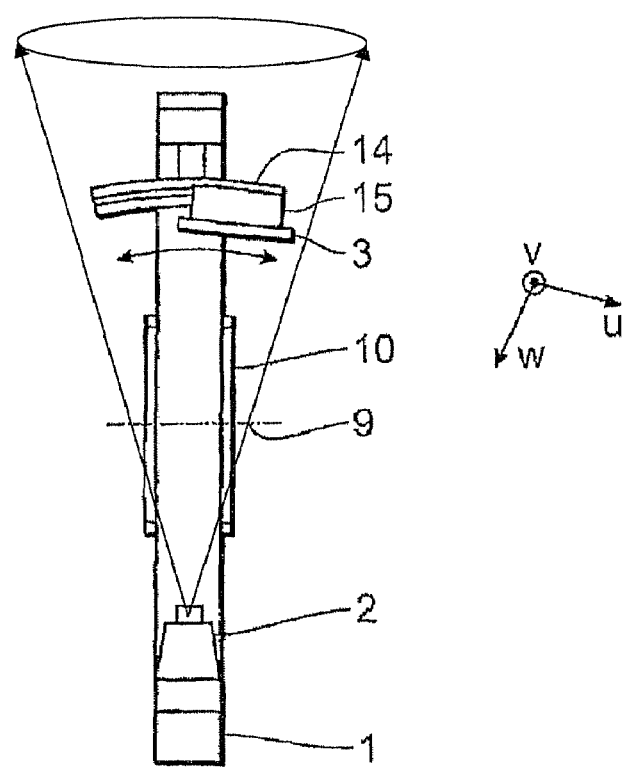
Figure 8:
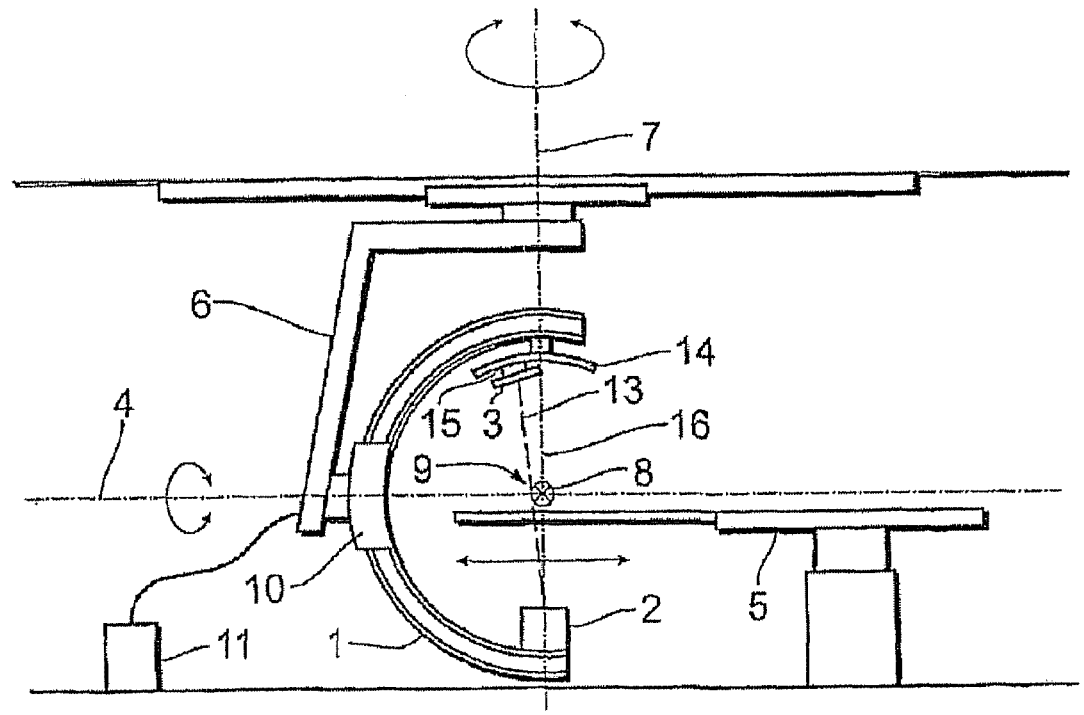

The invention will be described in detail hereinafter with reference to the drawings. Therein:

FIGS. 1a, b show a first embodiment of an X-ray apparatus in accordance with the invention, FIGS. 2 to 6 show different trajectories which can be adjusted by means of the X-ray apparatus in accordance with the invention, and FIGS. 7 and 8 are different views of a second embodiment of an X-ray apparatus in accordance with the invention.

FIG. 1a shows a first embodiment of an X-ray apparatus in accordance with the invention. In this C-arm X-ray apparatus an X-ray source 2 and an X-ray detector 3 are mounted at opposite ends of the C-arm 1. The C-arm 1 is journaled so as to be rotatable about a propeller axis 4 and a C-arm axis 9, that is, by way of a C-arm mount 10. The C-arm axis is oriented perpendicularly to the plane of drawing and passes through an isocenter 8 in this Figure. The C-arm 1 is journaled, by way of an L-arm 6, so as to be rotatable around an L-arm axis 7. A control unit 11 is provided for control of the X-ray apparatus. In order to enable the acquisition of cone beam projections, the object to be examined, for example, a patient, is arranged on a patient table 5 in such a manner that the longitudinal axis of the patient coincides with the propeller axis 4 in the position of the C-arm 1 shown.

A C-arm X-ray apparatus of this kind is often used for the acquisition of a set of cone beam projections of the examination zone of a patient while the X-ray source is moved along a predetermined trajectory around the examination zone. A 3D image of the examination zone can then be reconstructed from the acquired sets of cone beam projections. The shape of the cone beam is then determined by the shape of the sensitive detector surface, by the distance between the X-ray source and the X-ray detector and by a collimator possibly present between the X-ray source and the patient. The distance between the X-ray source and the isocenter typically amounts to approximately 80 cm whereas the distance between the detector and the isocenter typically amounts to approximately 40 cm. Nowadays use is often made of an X-ray detector in the form of an X-ray image intensifier which customarily has a circular sensitive detector surface whose diameter usually does not exceed 40 cm. In future, however, more and more use will be made of flat dynamic X-ray detectors having a rectangular sensitive detector surface which, for example, has the dimensions 40 cm×30 cm.

C-arm X-ray apparatuses are generally constructed so as to be isocentric. As a result, the trajectory of the X-ray source is limited to an isocentric spherical envelope. The central X-ray from the X-ray source to the X-ray detector then always passes through the isocenter. The trajectory of the X-ray detector is determined by the trajectory of the X-ray source. The longitudinal axis of a patient arranged on a patient table will be referred to hereinafter as the object axis. The direction perpendicularly to this object axis will be referred to as the transverse direction hereinafter.

The shape of the cone beam and the trajectory determine the largest volume whose contents can be reconstructed with adequate accuracy. This volume is referred to as the reconstructable volume. The volume to be reconstructed has to be distinguished therefrom. These two volumes may be but need not be identical. The volume to be reconstructed should be chosen as a sub-volume of the reconstructable volume.

Figure 1B:
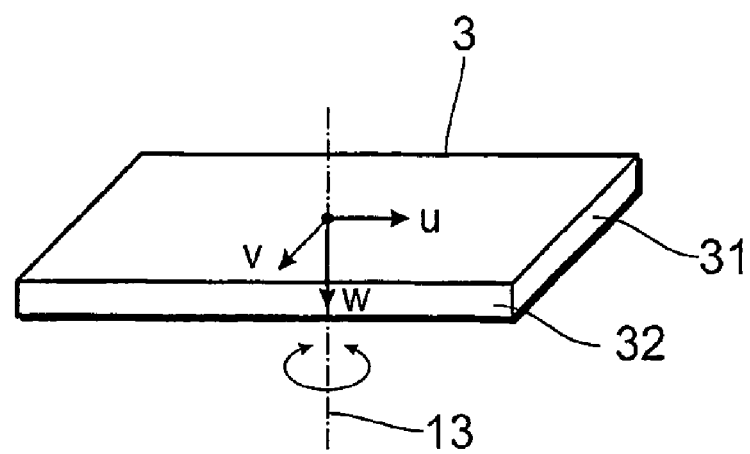
Figure 2:
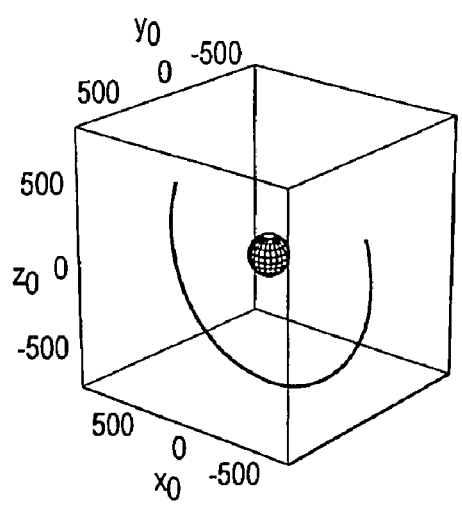

For practical reasons the trajectory is often configured as an arc of circle which extends through the isocenter in the transverse plane and encloses an angle of approximately 220°. A trajectory of this kind is shown in FIG. 2. It can be realized by rotating the C-arm either about the C-arm axis or about the propeller axis of the X-ray apparatus. In the first case the L-arm of the C-arm X-ray apparatus is arranged at the side of the patient whereas in the second case it is arranged at the head of the patient. When the detector is an X-ray image intensifier, the reconstructable volume is identified as the largest isocentric sphere covered by all cone beams along the arc of circle. The diameter of this sphere typically amounts to from 20 to 30 cm. When the X-ray detector is a flat dynamic detector, the longer edge of the rectangular detector surface is oriented either perpendicularly or parallel to the C-arm axis. For the trajectory shown in FIG. 1 the longer edge then extends either perpendicularly or parallel to the object axis. In this case the reconstructable volume comprises the large isocentric, longitudinally oriented cylinder covered by all cone beams along the circular trajectory. The diameter of this cylinder typically amounts to from 20 to 30 cm and its length from 15 to 20 cm.

In both cases the volume to be reconstructed is chosen to be identical to the reconstructable volume. The reconstruction itself is performed by means of the Feldkamp, Davis and Kress algorithm; the fact must be taken into account that the trajectory is not a complete circle and that in practice it also deviates to some extent from the ideal trajectory. It is also necessary to take into account the fact that the cone beam does not cover the entire patient, so that the cone beam projections acquired in practice are truncated.

For an exact reconstruction of the contents of the reconstructable volume it is necessary for the measured data to represent accurate estimates of the line integrals of the X-ray attenuation coefficients of the patient along exactly known lines of integration. It is also necessary that the measured sets of cone beam projections are quantized and sampled accordingly. However an image reconstructed in this manner may still exhibit considerable degradations, notably at the edges of the reconstructable volume. They are due partly to the fact that in the case of a circular trajectory the so-called completeness condition is not satisfied and that the cone beam projections are truncated. The severity of degradations of this kind increases as a function of the angle of aperture of the cone beam in the case of an X-ray image intensifier or as a function of the angle of aperture of the cone beam in the longitudinal direction in the case of a flat, rectangular X-ray detector. These angles themselves are dependent on the dimensions of the detector.

According to said completeness condition each plane intersecting the volume to be reconstructed should also intersect the trajectory. More accurately speaking, interaction exists between a given trajectory and a given volume in respect of satisfying or not satisfying the completeness condition. A more detailed description of the completeness condition is given in the previously mentioned German patent application 100 63 442.7 (PHDE 000232) which is explicitly incorporated herein by way of reference.

Figure 3:
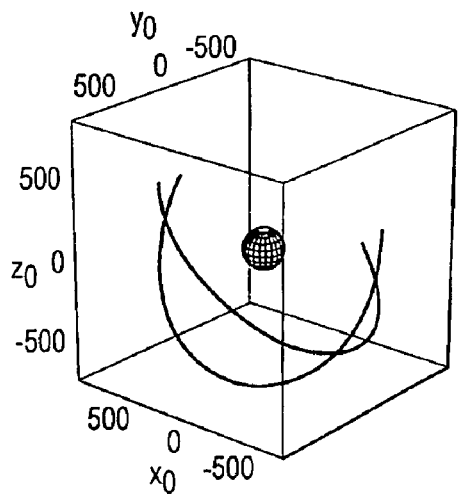
Figure 4:
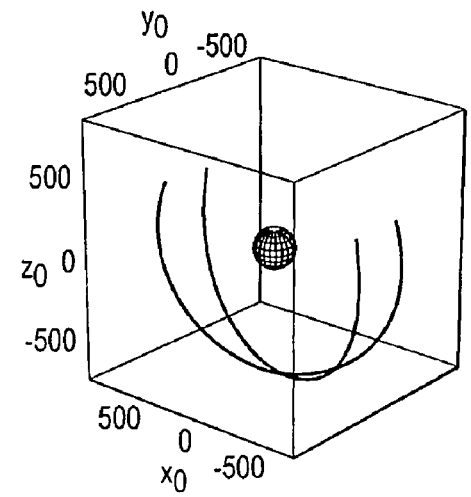

A planar trajectory, including an arc of circle, cannot be complete with respect to any volume. However, it is possible to use two arcs of circle whose axes intersect at the isocenter and enclose an angle as shown in FIG. 3. In this case the trajectory actually consists of two separate segments. Accordingly, the acquisition of the cone beam projections takes place in two runs. For the trajectory shown in FIG. 3 each arc of circle is produced by a rotation of the C-arm around its C-arm axis, the position of the C-arm mount being different each time. The L-arm is situated at the side of the patient. FIG. 4 shows an alternative possibility. Each arc of circle is now formed by a rotation around the propeller axis, the position of the L-arm being different each time. Use can also be made of trajectories which are complete and consist of only a single segment, so that only a single run is required. Such trajectories require a C-arm X-ray apparatus which enable a rotation of the C-arm axis during the run, that is, either around the propeller axis or around the L-arm axis. The FIGS. 5 and 6 show two examples of such trajectories. Trajectories of this kind and suitable X-ray apparatus for the use of such trajectories are also given in the cited German patent application 100 63 442.7 (PHDE 000232).

For a given non-planar trajectory and a given shape of the cone beam it is possible to find the largest volume for which said completeness condition is satisfied. In as far as the object to be examined fits completely within this volume, it can be reconstructed exactly. For non-planar trajectories this volume is then considered to be the reconstructable volume. Generally speaking, the reconstructable volume has a complex shape which is difficult to characterize explicitly.

However, if the X-ray detector is an X-ray image intensifier the reconstructable volume is again the largest isocentric sphere completely covered by all cone beams along the trajectory which in this case is not planar and preferably complete. Like in the case of the described arc of circle, the volume to be reconstructed will then be chosen to be identical to the reconstructable volume.

On the other hand, if the X-ray detector is a flat, rectangular X-ray detector, the reconstructable volume, generally speaking, is no longer an isocentric longitudinally oriented cylinder. Nevertheless, the volume to be reconstructed is preferably chosen as exactly as such a cylinder, because it corresponds to the three-dimensional imaging of a transverse thick slice of the patient. For a given reconstructable volume, an as large as possible isocentric, longitudinally oriented cylinder then exists within the reconstructable volume; this cylinder should be referred to as the reconstructable cylinder. Granted, it may also be attempted to perform a reconstruction outside the reconstructable cylinder or volume, but an increasing number of degradations will then be encountered outside the reconstructable volume.

For many trajectories, for example, the trajectories shown in the FIGS. 3 to 6, the longer edge of the detector is no longer oriented perpendicularly or parallel to the object axis during the completion of the trajectory. This leads to a reduction of the height or the diameter of the reconstructable cylinder. In the case of a given non-planar trajectory and preferred use of a flat, rectangular X-ray detector, in accordance with the invention the detector surface should, therefore, be oriented in such a manner that the dimensions of the reconstructable cylinder become maximum.

Therefore, in accordance with the invention the X-ray apparatus shown in FIG. 1a is provided with means 12 whereby the flat rectangular X-ray detector 3 can be rotated around the connecting line 13 extending between the focal point of the X-ray source 2 and the center of the X-ray detector 3. To this end, the means 12 may include, for example, a motor-driven joint which enables such a rotation of the X-ray detector in a plane perpendicular to the connecting line 13. The control device 11 is then constructed in such a manner that either the shorter edge 31 or the longer edge 32 (see FIG. 1b) of the rectangular detector 3 is always oriented perpendicularly to the object axis during the detection of the X-rays by the X-ray detector. The diameter of the reconstructable cylinder is maximized when the longer edge 32 of the X-ray detector 3 is continuously oriented at right angles to the object axis during the data acquisition. The length of the reconstructable cylinder is maximized when the longer edge 32 of the detector 3 is continuously oriented parallel to the object axis.

In order to specify the orientation of the X-ray detector 3 relative to the C-arm 1, there is introduced a right-handed Cartesian co-ordinate system having the co-ordinates x, y, z, its origin being situated in the isocenter 8, that is, the so-called laboratory system. The trajectory of the X-ray source 2 is described by a vector a(s) in the laboratory system, the parameter s describing the position along the trajectory. Analogously, the trajectory of the center of the rectangular detector 3 is described by a vector b(s). Furthermore, there is introduced a local, right-handed cartesian co-ordinate system having the two ordinates Q, V, W on the detector 3. The origin of this co-ordinate system is formed by the vector b(s). The u axis is directed along the longer edge 32 of the detector surface 3; the v axis is directed along the shorter edge 31 of the detector surface 3 and the w axis points towards the X-ray source 2, so that the w axis coincides with the central ray 13 of the cone beam. The axis of the C-arm 1 can be described by a unit vector in every position s. The isocentric plane, extending perpendicularly to this vector, is the so-called C-arm plane. The angle between the u axis and the C-arm plane corresponds to the plane of drawing in the position of the C-arm 1 shown. The angle between the u axis and the C-arm plane is denoted by the reference $\alpha(s)$. This angle is used to characterize the orientation of the X-ray detector 3 relative to the C-arm 1.

When the L-arm is present in the basic position shown in FIG. 1 during the completion of the trajectory, as is the case for the trajectory shown in FIG. 2, only two orientations are actually required and the selected orientation is maintained constant during the entire data acquisition. The first orientation is $\alpha(s)=0$, so that the longer edge 32 of the detector 3 is arranged parallel to the C-arm plane, and hence also parallel to the object axis, whereas the shorter edge 31 is situated perpendicularly to the C-arm plane and to the object axis. This is the case for the position of the C-arm 1 as shown in FIG. 1a.

The second orientation is $\alpha(s)=\pi/2$, the longer edge 32 then extending perpendicularly to the C-arm plane while the shorter edge 31 extends parallel to the C-arm plane. The longer edge 32 is then again situated parallel to the object axis, whereas the short edge 31 is again situated perpendicularly to the object axis. The choice of the two orientations is dependent on whether the circular trajectory is realized by a rotation around the C-arm axis 9 or around the propeller axis 4 and on whether the height of the reconstructable cylinder or its diameter is to be maximized.

If the L-arm is not situated in the basic position of FIG. 1 during the completion of the trajectory, as is the case for the trajectories shown in the FIGS. 3 to 6, generally speaking the orientation of the X-ray detector must be continuously readjusted during the data acquisition. The corresponding angle $\alpha(s)$, providing the desired orientation, is then calculated in advance during the definition of the trajectory. During the data acquisition the orientation of the X-ray detector 3 is then always adjusted correctly by means of the adjusting means 12 and the control unit 11, so that either the longer edge or the shorter edge of the X-ray detector is arranged perpendicularly to the object axis.

The FIGS. 7 and 8 show a second embodiment of an X-ray apparatus in accordance with the invention. FIG. 7 is a front view of the C-arm 1, that is, viewed from the propeller axis 4, while FIG. 8 is a side elevation of the X-ray apparatus. This embodiment is provided with means for moving the X-ray detector 3 "laterally" either along the u axis or the v axis from its central normal position (shown in FIG. 1a) relative to the position of the X-ray tube 2, without the entire C-arm 1 being moved. The X-ray detector 3 can thus be arranged asymmetrically relative to the central X-ray beam 16. The X-ray detector 3 is mounted, by way of example as shown in the FIGS. 7 and 8, on a rail 14 by way of a slide 15, which rail is curved in the form of an arc of circle around the focal point of the X-ray source 2. The curvature of the rail 14 then ensures that an anti-scatter grid (not shown) which is normally mounted on the X-ray detector 3 always remains focused on the X-ray tube.

The angle between the central axis 16 and the connecting line 13 between the focal point of the X-ray tube 2 and the center of the X-ray detector 3 can thus assume a value other than 0.

In the simplest and most general case, two runs are carried out through each segment of the trajectory, the X-ray detector 3 being shifted to one end of the rail 15 during the first run and to the other end during the second run. In each run half the number of required large cone beam projections is acquired each time, preferably with a slight overlap of the two halves. The two halves are then combined so as to produce effectively the data which would have been measured during a single run by means of an X-ray detector having twice the dimensions in the shift direction.

It is also possible to use more than two positions of the X-ray detector along the rail 14 and a correspondingly larger number of runs through each segment of the trajectory. It is also possible to construct the X-ray detector so that it is additionally rotatable, as shown in FIG. 1a, so that the X-ray detector can be shifted laterally as well as be rotated around its central axis while trajectories are being followed. Instead of using a curved rail 14, a straight rail could be used, for example, a rail extending parallel to the C-arm axis 9; in that case an anti-scatter grid would no longer be focused continuously.

The possibility for a lateral shift of the X-ray detector 3, as illustrated in the FIGS. 7 and 8, enables the desired effect of a large-area X-ray detector to be achieved by means of an X-ray detector having a significantly smaller surface area. This allows for a reconstructable cylinder which is large enough to enclose completely a transverse thick slice of the patient. Projections truncated in the transverse direction can thus be avoided to a high degree, without the detector surface being increased further.

In the embodiments of the X-ray apparatus shown, preferably an adjustable collimator is arranged between the X-ray source and the object to be examined. Furthermore, during the data acquisition the collimator should be adjusted in such a manner that only that part of the cone beam which can actually be incident on the detector is allowed to pass. Furthermore, it is advantageously arranged that the X-ray source emits a cone beam which is wide enough to completely irradiate the X-ray detector in all possible orientations and positions.

Furthermore, it may also be arranged that the detector is slidable along the central X-ray beam. The distance between the detector and the isocenter can thus be changed. This distance is kept constant while a trajectory is being completed.

The invention claimed is:

1. An X-ray apparatus which includes:
   an X-ray source for the emission of a conical X-ray beam;
   an X-ray detector for the multiple detection of the X-rays after their passage through an object to be examined, being arranged along an object axis, while the X-ray source and the X-ray detector are displaced along a trajectory;
   means for changing at least one of the position and the orientation of the X-ray detector relative to the X-ray source; and
   a control unit for displacing the X-ray source and the X-ray detector along the trajectory and for controlling, rotationally on a central axis of said beam, orientation of the X-ray detector during the detection of the X-rays, wherein the position and orientation of the X-ray detector relative to the X-ray source is over a range, and wherein the conical X-ray beam is wide enough to completely irradiate the X-ray detector over the entire range.

2. An X-ray apparatus which includes an X-ray source for the emission of a conical X-ray beam;
   and an X-ray detector for the multiple detection of the X-rays after their passage through an object to be examined, being arranged along an object axis, while the X-ray source and the X-ray detector are displaced along a trajectory, characterized in that the apparatus includes means for changing at least one of the position and the orientation of the X-ray detector relative to the X-ray source and also a control unit for displacing the X-ray source and the X-ray detector along the trajectory and for controlling at least one of the position and orientation of the X-ray detector during the detection of the X-rays, characterized in that the X ray apparatus includes a flat, rectangular X-ray detector which is rotatable around the connecting line extending between the focal point of the X-ray source and the center of the X-ray detector, the control unit for controlling the orientation of the X-ray detector being constructed in such a manner that one of the edges of the X-ray detector is always situated at right angles to the object axis while the trajectory is being completed, wherein the X-ray detector and the X-ray source are movably connected to each other by an arm.

3. An X-ray apparatus as claimed in claim 2, wherein for circular trajectories the control unit is arranged to adjust the orientation of the X-ray detector prior to the beginning of the completion of each trajectory in such a manner that one of the edges of the X-ray detector is situated at right angles to the object axis and that the orientation of the X-ray detector is kept constant while the trajectory is being completed.

4. An X-ray apparatus as claimed in claim 2, wherein the control unit is arranged to adjust the orientation in response to any change of the position of the X-ray source while a trajectory is being completed, and wherein the position and orientation of the X-ray detector relative to the X-ray source is over a range, and wherein the conical X-ray beam is wide enough to completely irradiate the X-ray detector over the entire range.

5. An X-ray apparatus which includes an X-ray source for the emission of a conical X-ray beam;
   and an X-ray detector for the multiple detection of the X-rays after their passage through an object to be examined, being arranged along an object axis, while the X-ray source and the X-ray detector are displaced along a trajectory, characterized in that the apparatus includes means for changing at least one of the position and the orientation of the X-ray detector relative to the X-ray source and also a control unit for displacing the X-ray source and the X-ray detector along the trajectory and for controlling at least one of the position and orientation of the X-ray detector during the detection of the X-rays, characterized in that the means for changing at least one of the position and the orientation of the X-ray detector are constructed in such a manner that the angle between the central ray of the X-ray beam and the connecting line extending between the focal point of the X-ray source and the center of the X-ray detector can assume a value other than zero, and that the control unit is constructed in such a manner that at least two different angular positions are adjusted during the detection of the X-rays, wherein the position and orientation of the X-ray detector relative to the X-ray source is over a range, and wherein the conical X-ray beam is wide enough to completely irradiate the X-ray detector over the entire range.

6. An X-ray apparatus as claimed in claim 5, wherein the X-ray detector is arranged on one or more rails in order to change at least one of its position and its orientation, and wherein the X-ray detector and the X-ray source are movably connected to each other by an arm.

7. An X-ray apparatus as claimed in claim 6, wherein in order to change at least one of its position and its orientation, the X-ray detector is mounted on a rail which extends essentially perpendicularly to the central ray, and wherein the rail is curved around the focal point of the X-ray source.

8. An X-ray apparatus as claimed in claim 5, wherein the X-ray detector is a flat, rectangular X-ray detector.

9. An X-ray apparatus as claimed in claim 5, wherein the control unit is arranged for the multiple displacement of the X-ray source along a trajectory during the irradiation of the object to be examined and for the adjustment of a different angular position of the X-ray detector during each completion of the same trajectory.

10. A method for forming X-ray images, comprising:
emitting, by an X-ray source, a conical X-ray beam for detection, by an X ray detector, of X-rays after their passage through an object to be examined while the X-ray source and the X-ray detector are displaced along a trajectory; and
in order to maximize a reconstructable examination zone, moving, during said detection, the X-ray detector so as to off-center position of the X-ray detector from said beam and so as to change orientation of the X-ray detector relative to the X-ray source, wherein a position and orientation of the X-ray detector relative to the X-ray source is over a range, and wherein the conical X-ray beam is wide enough to completely irradiate the X-ray detector over the entire range.

11. A computer program product having a computer readable medium in to which is embodied a computer program executable by a computer to perform the method of claim 10.

12. The method of claim 10, further comprising performing said moving off-center on a track.

13. The method of claim 12, wherein said track is curved to maintain the detector facing the source.

14. The method of claim 10, wherein said zone is in the shape of a cylinder.

15. A device for performing the method of claim 10, said device comprising said X ray source, said X ray detector, and a controller for said moving.

16. The X-ray apparatus of claim 5, including a flat, rectangular X-ray detector configured for rotation around the connecting line extending between the focal point of the X-ray source and the center of the X-ray detector, the control unit for controlling the orientation of the X-ray detector being constructed in such a manner that one of the edges of the X-ray detector is always situated at right angles to the object axis while the trajectory is being completed.

17. The X-ray apparatus of claim 6, including a flat, rectangular, non-square X-ray detector configured for rotation around the connecting line extending between the focal point of the X-ray source and the center of the X-ray detector, the control unit for controlling the orientation of the X-ray detector being constructed in such a manner that one of the edges of the X-ray detector is always situated at right angles to the object axis while the trajectory is being completed.

18. The X-ray apparatus of claim 7, including a flat, rectangular X-ray detector configured for rotation around the connecting line extending between the focal point of the X-ray source and the center of the X-ray detector, the control unit for controlling the orientation of the X-ray detector being constructed in such a manner that one of the edges of the X-ray detector is always situated at right angles to the object axis while the trajectory is being completed.

19. The X-ray apparatus of claim 8, including a flat, rectangular, non-square X-ray detector configured for rotation around the connecting line extending between the focal point of the X-ray source and the center of the X-ray detector, the control unit for controlling the orientation of the X-ray detector being constructed in such a manner that one of the edges of the X-ray detector is always situated at right angles to the object axis while the trajectory is being completed.

20. The X-ray apparatus of claim 9, including a flat, rectangular X-ray detector which is rotatable around the connecting line extending between the focal point of the X-ray source and the center of the X-ray detector, the control unit for controlling the orientation of the X-ray detector being constructed in such a manner that one of the edges of the X-ray detector is always situated at right angles to the object axis while the trajectory is being completed.

* * * * *